United States Patent
Jackson et al.

(10) Patent No.: US 6,890,324 B1
(45) Date of Patent: May 10, 2005

(54) TAMPON APPLICATOR

(75) Inventors: Dane R. Jackson, Bloomingdale, NJ (US); Paul A. Siracusa, Florida, NY (US); Keith Edgett, Ramsey, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/894,042

(22) Filed: Jun. 28, 2001

(51) Int. Cl.⁷ .............................................. A61F 13/20
(52) U.S. Cl. ................................ 604/385.17; 604/904
(58) Field of Search ............................. 604/11–18, 57, 604/59–60, 311, 904

(56) References Cited

U.S. PATENT DOCUMENTS

| | | | |
|---|---|---|---|
| 1,131,349 A | 3/1915 | Ellis | |
| 2,188,923 A | 2/1940 | Robinson | 128/285 |
| 2,264,586 A | 12/1941 | Ross | 128/285 |
| 2,476,956 A | 7/1949 | Bonham | 128/263 |
| 2,489,502 A | 11/1949 | Ruth | 128/270 |
| 2,509,241 A | 5/1950 | Mende | 128/270 |
| 2,587,717 A | 3/1952 | Fourness | 128/263 |
| 2,739,593 A | 3/1956 | McLaughlin | 128/263 |
| 2,854,978 A | 10/1958 | Millman et al. | 128/285 |
| 2,922,423 A | 1/1960 | Rickard et al. | 128/263 |
| 2,934,068 A | 4/1960 | Graham, Jr. et al. | 128/263 |
| 3,034,508 A | 5/1962 | Nalle | 128/263 |
| 3,059,642 A | 10/1962 | Gershen | 128/263 |
| 3,068,867 A | 12/1962 | Bletzinger et al. | 128/285 |
| 3,086,527 A | 4/1963 | Forrest | 128/263 |
| 3,090,385 A | 5/1963 | Brecht | 128/263 |
| 3,101,713 A | 8/1963 | Sargent | 128/263 |
| 3,103,929 A | 9/1963 | Brecht | 128/263 |
| 3,124,134 A | 3/1964 | Gardner | 128/263 |
| 3,148,680 A | 9/1964 | Roberts et al. | 128/263 |
| 3,351,060 A | 11/1967 | Woskin | 128/263 |
| 3,409,011 A | 11/1968 | Mittag | 128/263 |
| 3,429,312 A | 2/1969 | Stump | 128/263 |
| 3,575,169 A | 4/1971 | Voss et al. | 128/263 |
| 3,628,533 A | 12/1971 | Loyer | 128/263 |
| 3,645,263 A | 2/1972 | Bates | 128/263 |
| 3,674,026 A | 7/1972 | Werner et al. | 128/263 |
| 3,765,417 A | 10/1973 | Crockford | 128/263 |
| 3,805,786 A | 4/1974 | Bernardin et al. | 128/263 |
| 3,807,399 A | 4/1974 | Morman et al. | 128/263 |

(Continued)

FOREIGN PATENT DOCUMENTS

| | | |
|---|---|---|
| JP | Sho 53-74795 | 7/1978 |
| JP | 57-87730 U | 11/1980 |
| ZA | 777411 | 11/1977 |

OTHER PUBLICATIONS

Entry and Order Granting Defendants' Motion for Summary Judgment of Non–Infringement Based on Markman Ruling. (Doc. 95). Nov. 3, 2003.

(Continued)

Primary Examiner—John J. Calvert
Assistant Examiner—Michele Kidwell
(74) Attorney, Agent, or Firm—Ohlandt, Greeley, Ruggiero & Perle, LLP

(57) ABSTRACT

A tampon is provided having an applicator barrel adapted to house a pledget, and especially a radially expanding pledget, and receive a telescoping plunger that is adapted to expel the pledget from the barrel. The applicator barrel has a finger-grip area with at least one set of diametrically opposed, substantially flattened surfaces, convex surfaces, concave surfaces, or any combination thereof. These surfaces have at least one gripping structure to enhance the gripping characteristics of the applicator, allowing the user to securely hold the applicator during insertion and removal and during expulsion of the pledget from the barrel.

32 Claims, 15 Drawing Sheets

U.S. PATENT DOCUMENTS

| | | | |
|---|---|---|---|
| 3,831,605 A | 8/1974 | Fournier | 128/263 |
| 3,834,389 A | 9/1974 | Dulle | 128/285 |
| 3,835,856 A | 9/1974 | Warncke | 128/263 |
| 3,895,634 A | 7/1975 | Berger et al. | 128/263 |
| D250,663 S | 12/1978 | Koch et al. | D24/99 |
| 4,182,328 A | 1/1980 | Boldue et al. | 128/235 |
| 4,198,978 A | 4/1980 | Nigro | 128/285 |
| 4,269,187 A | 5/1981 | Sakurai et al. | 128/263 |
| 4,276,881 A | 7/1981 | Lilaonitkul | 128/263 |
| 4,318,405 A | 3/1982 | Sneider | 128/263 |
| 4,361,150 A | 11/1982 | Voss | 128/263 |
| 4,411,647 A | 10/1983 | Sakurai et al. | 604/16 |
| 4,412,833 A | 11/1983 | Wiegner et al. | 604/14 |
| 4,424,054 A | 1/1984 | Conn et al. | 604/11 |
| 4,479,791 A | 10/1984 | Sprague | 604/14 |
| 4,536,178 A | 8/1985 | Lichstein et al. | 604/15 |
| 4,543,086 A | 9/1985 | Johnson | 604/11 |
| 4,573,963 A | 3/1986 | Sheldon | 604/15 |
| 4,573,964 A | 3/1986 | Huffman | 604/15 |
| 4,891,042 A | 1/1990 | Melvin et al. | 604/18 |
| 5,290,501 A | 3/1994 | Klesius | 264/322 |
| 5,395,308 A | 3/1995 | Fox et al. | 604/15 |
| D415,565 S | 10/1999 | Hayes et al. | D24/141 |
| 6,045,526 A | 4/2000 | Jackson | 604/15 |

OTHER PUBLICATIONS

Memorandum Opinion, Jun. 4, 2002.

Report of Evan Hutchison Pursuant to Fed. R. Civ. Proc. 26(a)(2), Oct. 30, 2002.

Rebuttal Expert Report of Evan Hutchison, Dec. 27, 2002.

Supplemental Expert Report of Evan Hutchison, Jun. 27, 2003.

First Expert Report of Mario Turchi, Oct. 30, 2002.

Supplemental Expert Report of Mario Turchi, Jun. 27, 2003.

Rebuttal Expert Report of Mario A. Turchi, Dec. 27, 2002.

Rebuttal Expert Report of Mario A. Turchi, Defendant's Exhibit 40, Apr. 2, 2003.

Expert Report of G.A.M. Butterworth, Nov. 22, 2002.

Rebuttal Expert Report of G.A.M. Butterworth, Jan. 19, 2003.

Expert Report of James Moller, Ph.D., P.E., Nov. 26, 2002.

Playtex Products, Inc. v. Proctor & Gamble Co. and Proctor & Gamble Distributing Co., Appeal from the US District Court for the Southern District of Ohio in Case No. 02–CV–00391, District Judge Thomas M. Rose, Non–Confidential Joint Appendix, Jun. 9, 2004.

Playtex Products, Inc. v. Proctor & Gamble Co. and Proctor & Gamble Distributing Co., Appeal from the US District Court for the Southern District of Ohio in Case No. 02–CV–00391, District Judge Thomas M. Rose, Non–Confidential Reply Brief of Appellant, May 28, 2004.

Playtex Products, Inc. v. Proctor & Gamble Co. and Proctor & Gamble Distributing Co., Appeal from the US District Court for the Southern District of Ohio in Case No. 02–CV–00391 District Judge Thomas M. Rose, Non–Confidential Brief for Defendants–Appellees the Proctor & Gamble Company and the Procter & Gamble Distributing Company, May 12, 2004.

Playtex Products, Inc. v. Proctor & Gamble Co. and Proctor & Gamble Distributing Co., Appeal from the US District Court for the Southern District of Ohio in Case No. 02–CV–00391, District Judge Thomas M. Rose, Non–Confidential Brief of Appellant, Apr. 2, 2004.

Playtex Products, Inc. v. Proctor & Gamble Distributing Co. et al., District Judge Thomas M. Rose, Supplemental Expert Report of G.A.M. Butterworth, Case No. C–1–02–391, Aug. 20, 2003.

Playtex Products, Inc. v. Proctor & Gamble Distributing Co. et al., District Judge Thomas M. Rose, Supplemental Report of James C. Moller, Ph.D., P.E., Case No. C–1–02–391, Aug. 15, 2003.

TAMPON APPLICATOR

BACKGROUND OF THE INVENTION

1. Field of the Invention

The present invention relates to catamenial insertion devices. More particularly, the present invention relates to a catamenial insertion device, such as a tampon applicator, having a fingergrip area with at least one gripping structure.

2. Description of the Prior Art

A catamenial insertion device or applicator normally has two components, namely a barrel and a plunger that is adapted to telescopically slide in the barrel. The material to be expelled, such as an absorbent pledget, is positioned in the barrel of the applicator. The barrel has a first end for ejection of the pledget, and a second end for receipt of the plunger. To use the tampon applicator, the consumer will position the ejection end appropriately, grasp the barrel, and move or slide the plunger in the barrel towards the ejection end of the barrel to expel the pledget.

Tampon pledgets, and notably radially expanding pledgets, due to their design, exert a pressure or friction force on the, inside wall of the applicator barrel. Thus, expulsion of the pledget from the barrel requires an applicator with a gripping configuration conducive to secure holding by the user with minimal pressure being applied to the barrel. The significance of minimizing pressure on the barrel of the applicator is that deformation of the barrel is reduced. Such barrel deformation causes significant friction amongst the pledget, barrel, and plunger, thereby significantly impeding the expulsion of the pledget from the barrel.

Various configurations for fingergrip areas on the barrel of an applicator have been proposed to facilitate handling and placement of the applicator, and expulsion of the pledget. One approach is a tampon applicator having an integral fingergrip that is formed by embossing an outside surface of the barrel of the applicator. The embossed portion of the applicator barrel typically takes the form of a series of raised circumferential rings or a series of discrete raised dots aligned in several circumferential rows. Examples of such fingergrips can be found in U.S. Pat. No. 6,045,526 to Jackson, U.S. Pat. No. 5,395,308 to Fox et al., U.S. Pat. No. 5,290,501 to Klesius, U.S. Pat. No. 4,573,964 to Huffman; U.S. Pat. No. 4,573,963 to Sheldon; U.S. Pat. No. 4,891,042 to Nelvin et al.; U.S. Pat. No. 4,412,833 to Wiegner et al.; U.S. Pat. No. 3,895,634 to Berger; U.S. Pat. No. 3,628,533 to Leyer; U.S. Pat. No. 2,922,423 to Rickard et al; U.S. Pat. No. 2,587,717 to Fourness; and U.S. Pat. No. 2,489,502 to Ruth.

Another approach to the gripping problem is found in U.S. Pat. No. 3,575,169 to Voss et al., which provides separate raised elements that are applied to an outer tube of a tampon applicator to provide a fingergrip. The elements can be formed of plastic, rubber, ceramic, or other materials, and can either be affixed to the outer tube by interference fit or by bonding.

U.S. Pat. No. 4,536,178 to Lichstein et al. discloses a tampon applicator having flattened surfaces with a gripping structure on the flattened surface. However, the gripping structure disclosed is limited to rows of ribs.

Thus, there is a need for a tampon applicator with a distinct fingergrip area having at least one gripping structure, other than ribs, that allows a consumer to easily grip the applicator or applicator barrel and expel the pledget with ease, especially overcoming the increased expulsion forces associated with a radially expanding pledget in the barrel.

SUMMARY OF THE INVENTION

It is an object of the present invention to provide a tampon applicator or applicator barrel having a distinct fingergrip area with at least one gripping structure.

It is another object of the present invention to provide such a tampon applicator barrel where the fingergrip area is substantially flattened.

It is yet another object of the present invention to provide such a tampon applicator barrel in which the substantially flattened fingergrip area results in a finger and a thumb hold that enables the user to overcome the expulsion force exerted on the applicator barrel.

It is still another object of the present invention to provide such a tampon applicator barrel where the at least one gripping structure is selected from the group consisting of embossments, protuberances other than ribs, slits, grooves, louvers, perforations, lances, abrasive media, high wet coefficient of friction material, pressure sensitive adhesive, or any combinations thereof.

It is a further object of the present invention to provide such a tampon applicator barrel where the at least one gripping structure may be raised, depressed, tilted, aligned with the outer surface of the barrel, or any combinations thereof.

These and other objects of the present invention will be appreciated from a tampon having an applicator barrel adapted to house a pledget, and especially a radially expanding pledget, and to receive a plunger that is adapted to expel the pledget from the barrel. The applicator barrel has a fingergrip area with at least one set of diametrically opposed, substantially flattened, convex, or concave surfaces. These surfaces have at least one gripping structure to enhance the gripping characteristics of the applicator. The fingergrip area with at least one gripping structure allows the user to hold securely the applicator during insertion and removal, and more importantly, during expulsion of the pledget from the barrel.

DETAILED DESCRIPTION OF THE INVENTION

Figure 1:
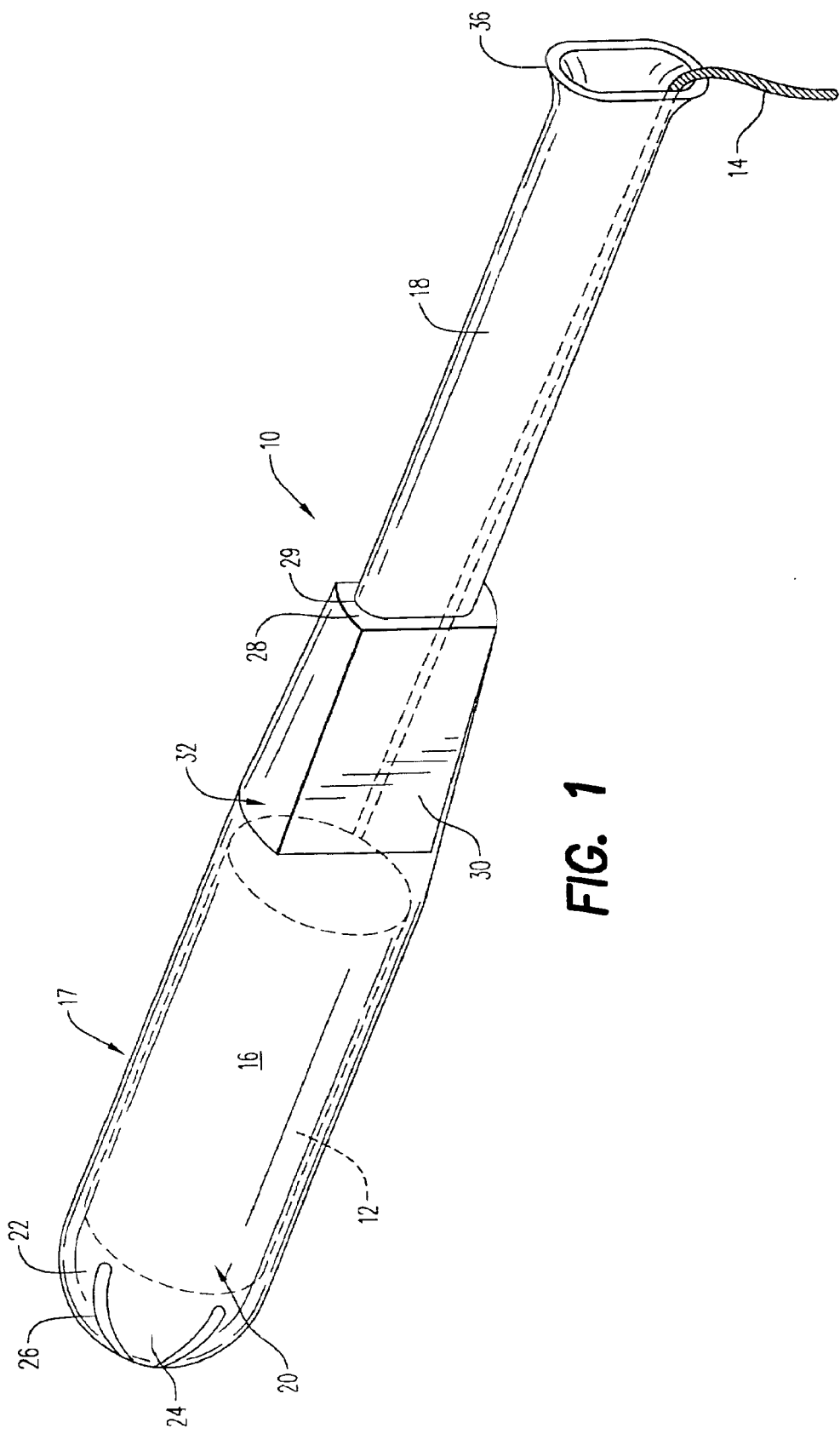
FIG. 1 is a perspective view of one embodiment of the tampon applicator according to the present invention.

Referring to the drawings and, in particular, FIG. 1, there is shown a tampon applicator or inserter generally represented by reference numeral 10. Tampon applicator 10 houses and carries a tampon pledget 12 having a removal string 14. Tampon applicator 10 has a barrel 16 and a plunger 18 telescopically engageable with the barrel.

The plunger 18 is adapted to eject the pledget 12 from the barrel 16 out of the ejection end 20 of the barrel into the vagina of a user. The barrel 16 has a central body 17 that is preferably tubular and is adapted to house and carry the pledget 12 therein. The barrel 16 has a forward or ejection end 20, and an opposite, rear or plunger-receiving end 32.

The ejection end 20 of barrel 16 can be open or can have a dome shape. The ejection end 20 preferably has a hemispherical, dome-shaped tip 22. The tip 22 may include a plurality of petals 24, which are preferably formed by a plurality of slits 26. The petals 24 are flexible, enabling the pledget 12 to be ejected therethrough when the plunger 18 is pressed against the top of the pledget 12 within the barrel 16.

The plunger-receiving end 32 of barrel 16 has a decreased or tapered width or diameter relative to central body 17 of the barrel, which serves as a transition between the body and the rearmost plunger edge 28. Receiving end 32 can have one or more substantially flattened surfaces, which form the fingergrip area. Preferably, receiving end 32 has one or more pairs of diametrically opposed, substantially flattened surfaces. In one embodiment of the present invention, as shown in FIG. 1, receiving end 32 has one pair of diametrically opposed, substantially flattened surfaces 30, which form a generally rectangular fingergrip area.

Figure 2:
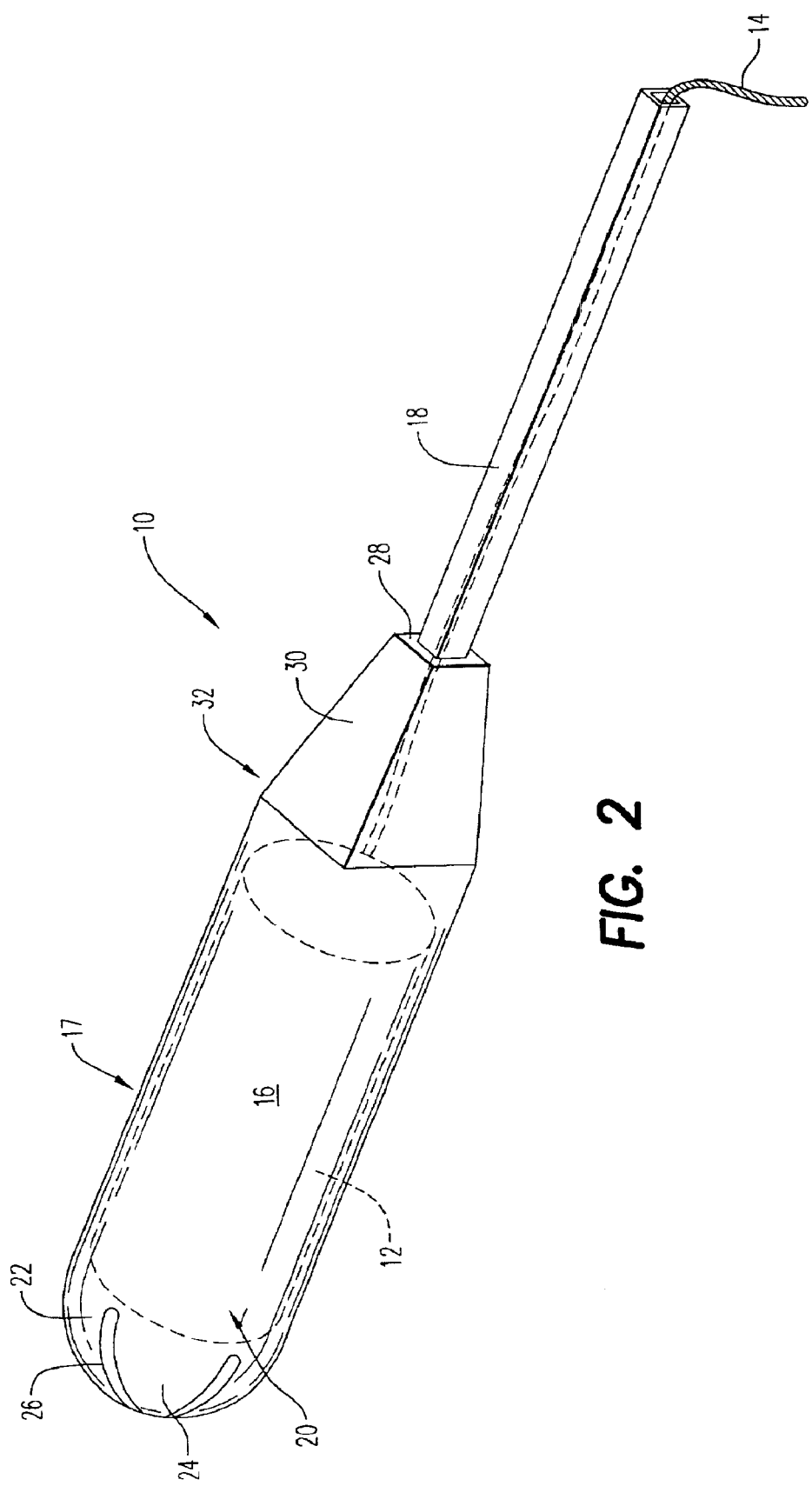
FIG. 2 is a perspective view of another fingergrip embodiment of the tampon applicator according to the present invention.

Referring to FIG. 2, receiving end 32 has two pairs of diametrically opposed, substantially flattened surfaces 30, which have a reduced diameter from central body 17 to plunger edge 28. The two pairs of substantially flattened surfaces form a generally square cross-section. Plunger 18 is also shown as having a generally square cross-section.

Figure 3:
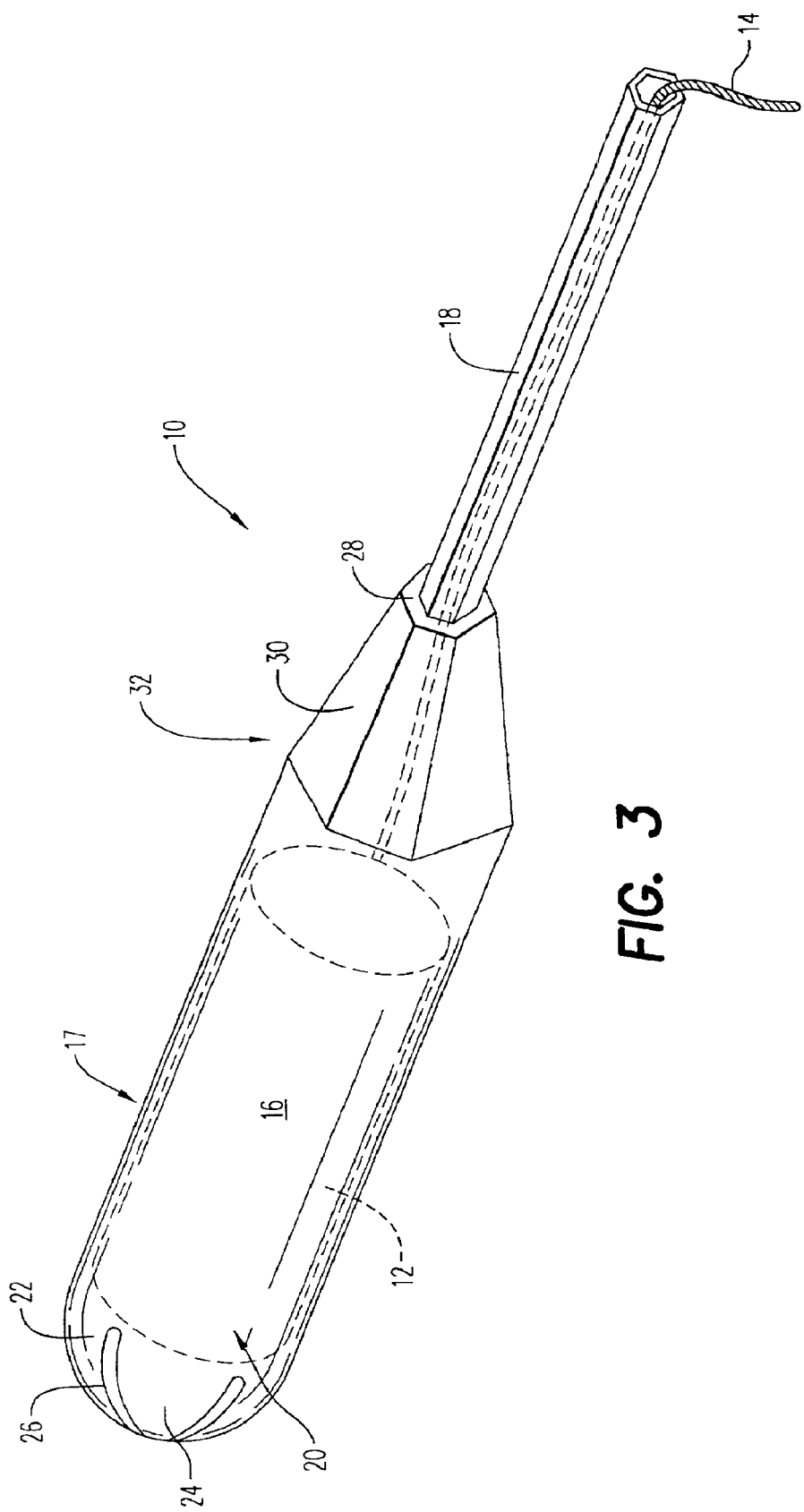
FIG. 3 is a perspective view of another fingergrip embodiment of the tampon applicator according to the present invention.

Referring to FIG. 3, receiving end 32 has three pairs of diametrically opposed, substantially flattened surfaces 30, which have a reduced diameter from central body 17 to plunger edge 28. The three pairs of diametrically opposed, substantially flattened surfaces 30 form a generally hexagonal cross-section, which results in superior gripping ability. Plunger 18 is also shown as having a generally hexagonal cross-section.

Figure 4:
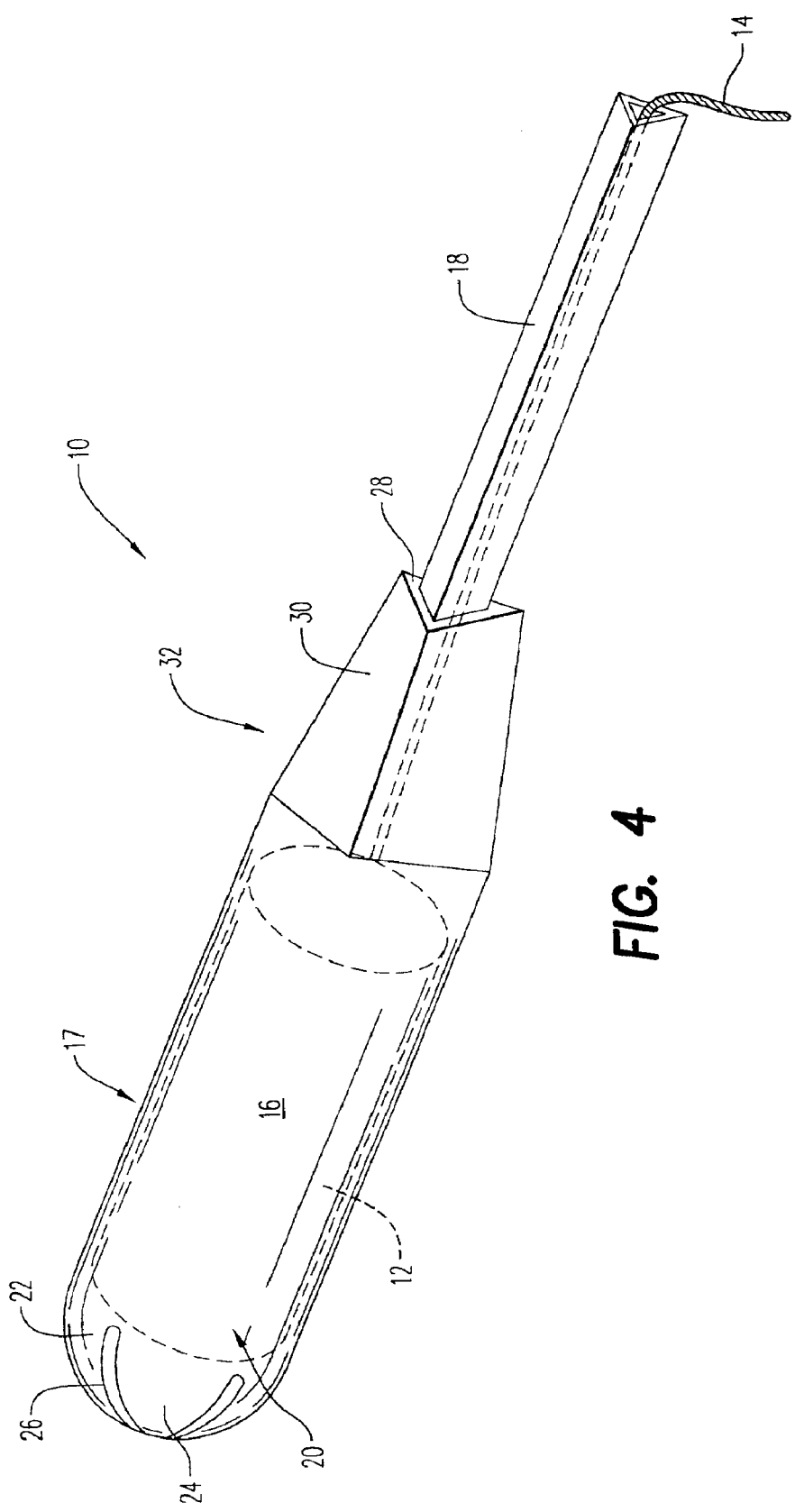
FIG. 4 is a perspective view of another fingergrip embodiment of the tampon applicator according to the present invention.

Referring to FIG. 4, applicator 10 of the present invention has three substantially flattened surfaces 30 formed on receiving end 32. The three substantially flattened surfaces have a reduced diameter from central body 17 to plunger edge 28 and form a generally triangular fingergrip area. Plunger 18 is also shown as having a generally triangular cross-section.

It should be understood that the present invention is not limited to the number of pairs of diametrically opposed, substantially flattened surfaces depicted in FIGS. 1 through 3, or the number of substantially flattened surfaces depicted in FIG. 4. Applicator 10 can be formed with any number of substantially flattened surfaces, pairs of diametrically opposed, substantially flattened surfaces, or any combinations thereof suitable for forming a fingergrip area on the receiving end of the barrel.

By forming a fingergrip area on the receiving end 32 of barrel 16, where there is no pledget housed, a more rigid construction results. This rigidity is further enhanced due to the fact that the plunger also has a reduced diameter. As a result, the walls of the barrel between the receiving end 32 and the plunger edge 28 are substantially thick, and thus rigid. The rigidity not only results in a stronger construction, it reduces and/or eliminates deformation of the barrel, and subsequently reduces frictional forces amongst the barrel, plunger, and pledget during use. This reduction in frictional forces results in a greater ease of insertion of the applicator and expulsion of the pledget from the barrel of the applicator into the vagina.

Figure 5:
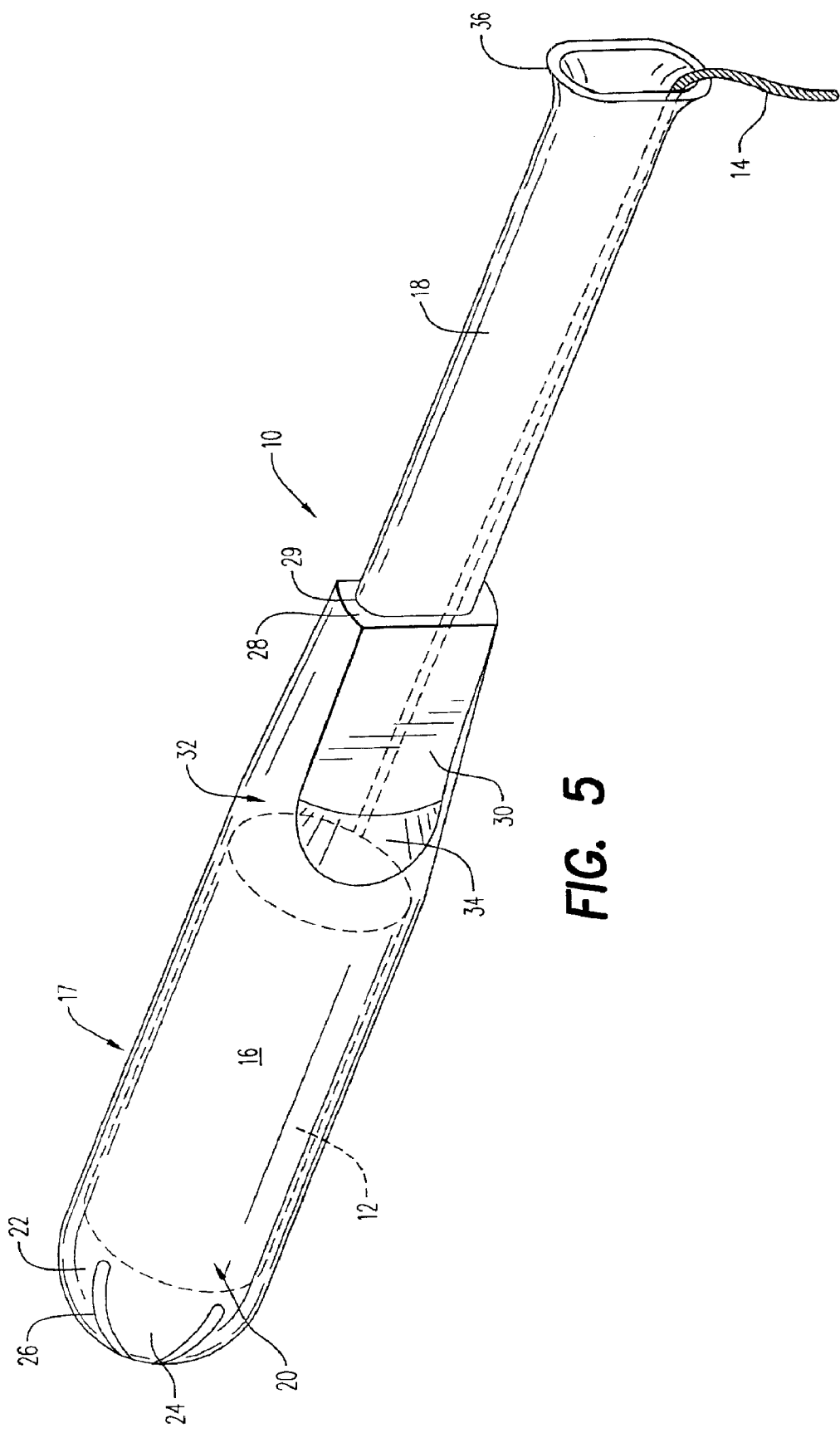
FIG. 5 is a perspective view of one embodiment of the tampon applicator of FIG. 1 having gripping structures according to the present invention.

In another embodiment of the present invention, as shown in FIG. 5, receiving end 32 of applicator 10 has one pair of diametrically opposed, substantially flattened surfaces 30 and two angled shoulder surfaces 34. The shoulder surfaces 34 form a finger and/or thumb hold or grip.

The angled shoulders 34 transcend from the barrel 16 to the flattened surfaces 30 and, thus, have a reduced diameter relative to the ejection end 20. The angled surface of the shoulders 34 can vary from almost 0° to almost 90° relative to the length of the barrel 16. To further enhance grasping of the barrel 16, the two substantially flattened surfaces 30 are generally decreasingly tapered from the angled shoulders 34 to the plunger edge 28. Accordingly, the angled shoulder surfaces 34 of the receiving end 32 provide an area on which the middle finger and thumb of a user may push off or rest on during the grasping of the applicator 10 and insertion of the applicator and pledget 12 into the vagina of a user. It should be understood that while FIG. 5 is depicted with two angled shoulders 34, applicator 10 could have at least two angled shoulders 34. The number of angled shoulders can correspond to the number of flattened surfaces formed on applicator 10.

Figure 13:
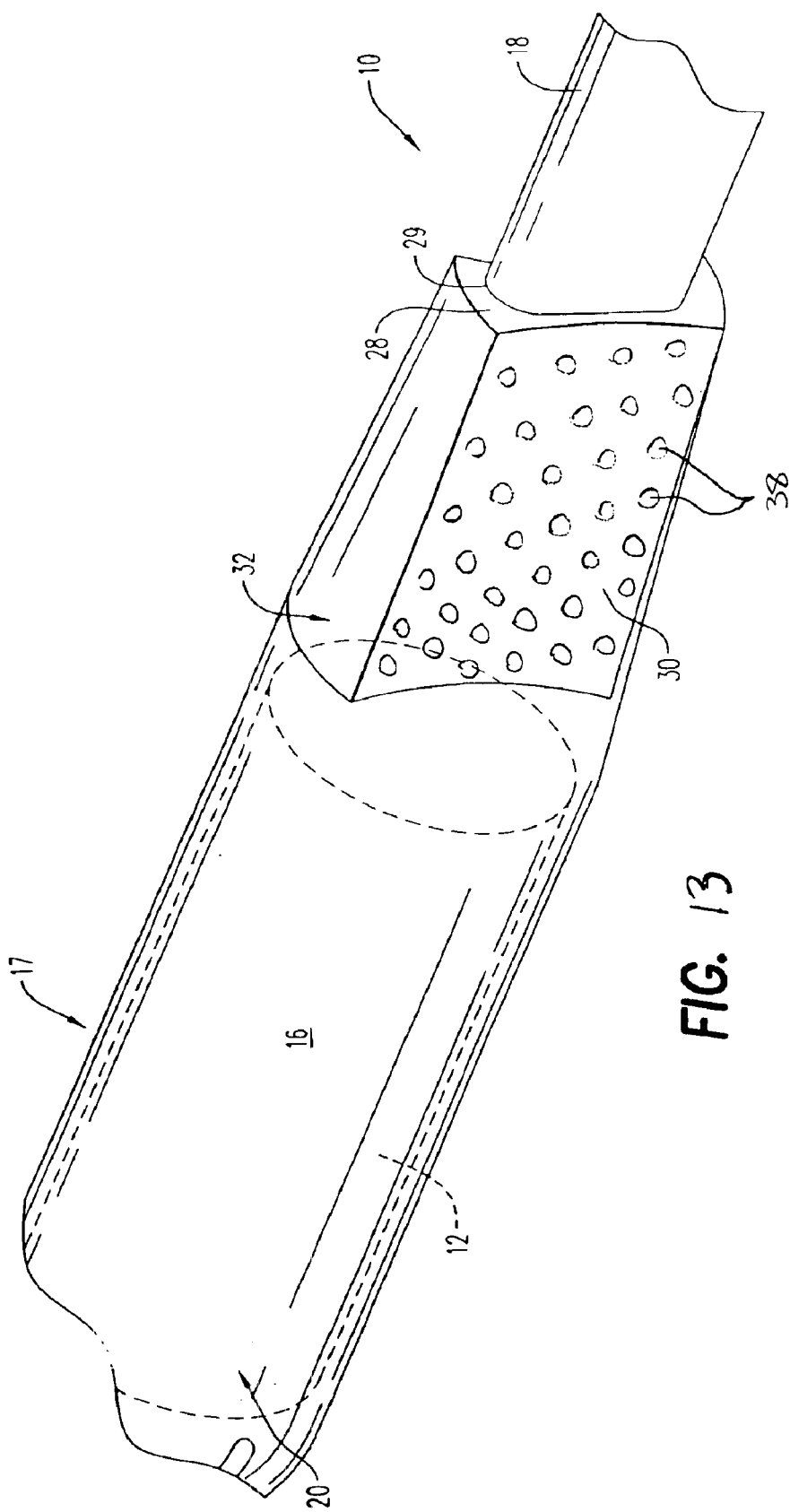
FIG. 13 is a perspective view of the tampon applicator of FIG. 8 with gripping structures according to an embodiment of the present invention.
Figure 14:
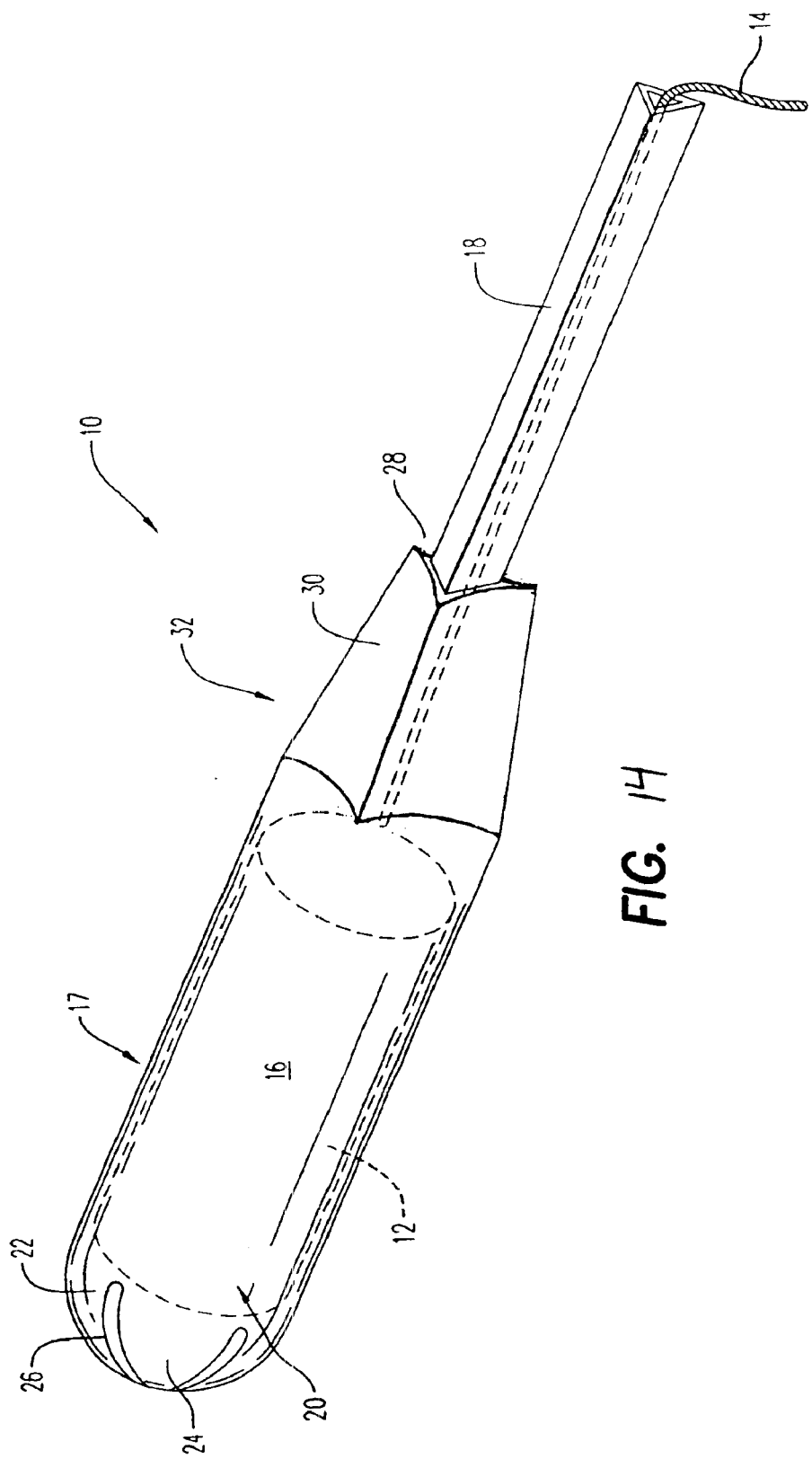
FIG. 14 is a perspective view of the tampon applicator of FIG. 4 with an odd number of concave surfaces according to an embodiment of the present invention.
Figure 15:
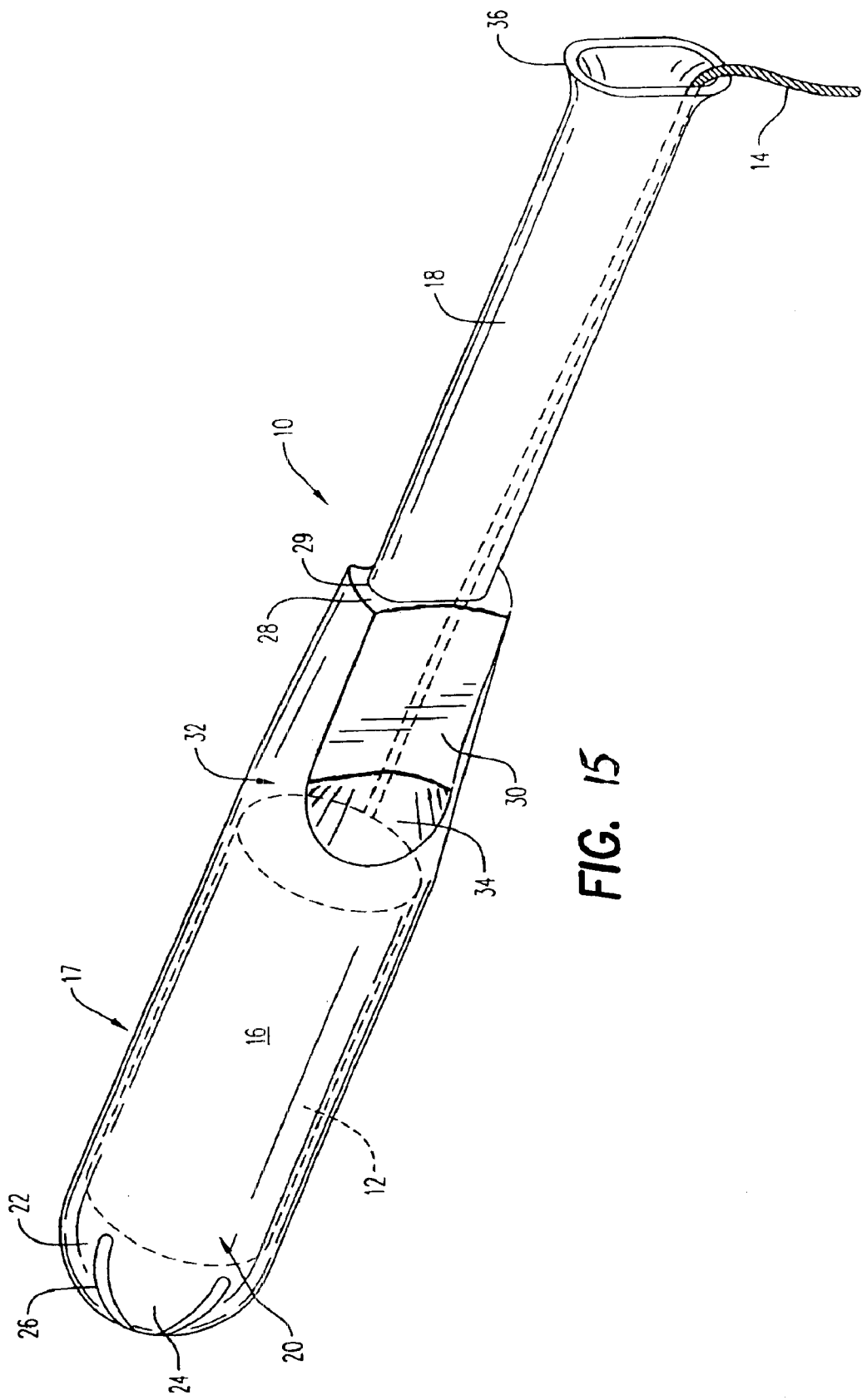
FIG. 15 is a perspective view of the tampon applicator of FIG. 5 with concave surfaces according to an embodiment of the present invention.

In an alternative embodiment of the applicator of FIGS. 1 through 5 of the present invention, at least one, and more preferably a plurality, of gripping structures are disposed on the surfaces 30. While these alternative embodiments are discussed below with respect to FIG. 1, they can be equally applied to the fingergrip area of FIGS. 2 through 5, 8 and 9. Examples of such are depicted in FIGS. 10 and 13.

The gripping structures may be, for example, one or more embossments, protuberances other than ribs, slits, grooves, perforations, lances, abrasive media, high wet coefficient of friction material, pressure sensitive adhesive, or any combinations thereof. The gripping structures may be raised above surfaces 30, depressed below surfaces 30, constructed so as the top of the gripping structure aligns with the outer surface of surfaces 30, tilted towards or away from surfaces 30, or any combinations thereof. The gripping structures may be patterned or arranged in any configuration, and in any number suitable for creating an enhanced gripping area for a user's fingers.

Figure 6:
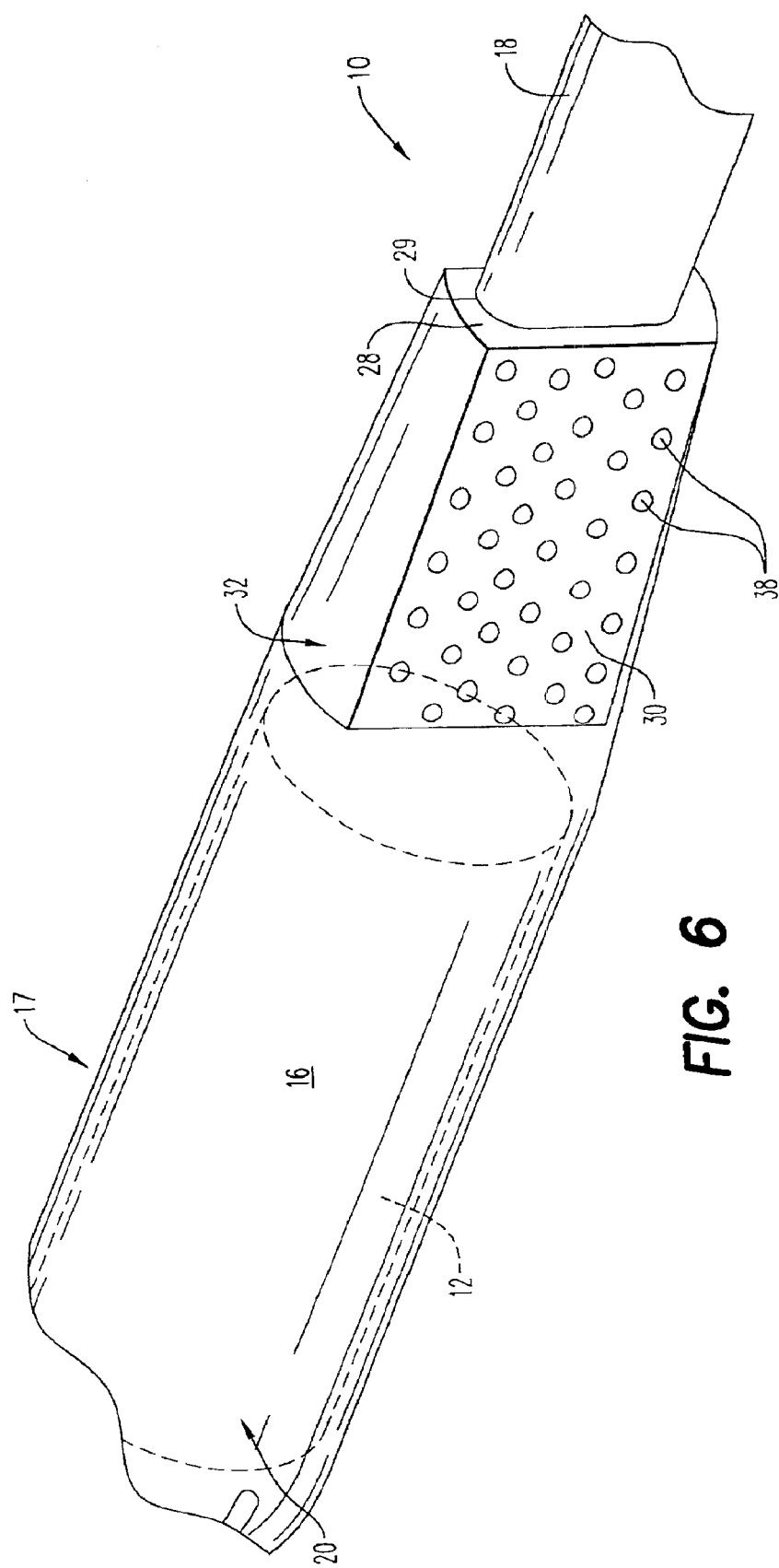
FIG. 6 is a perspective view of another embodiment of the tampon applicator of FIG. 1 having gripping structures according to the present invention.

Referring to FIG. 6, by way of example, one embodiment of the at least one gripping structure of the fingergrip area of tampon applicator 10 of the present invention is shown having a plurality of circular shaped gripping structures 38 disposed on substantially flattened surfaces 30. These circular shaped gripping structures may be raised above surfaces 30, depressed below surfaces 30, through or virtually through surfaces 30, or a combination thereof. Also, the gripping structures can be disposed in any suitable pattern or number.

Figure 7:
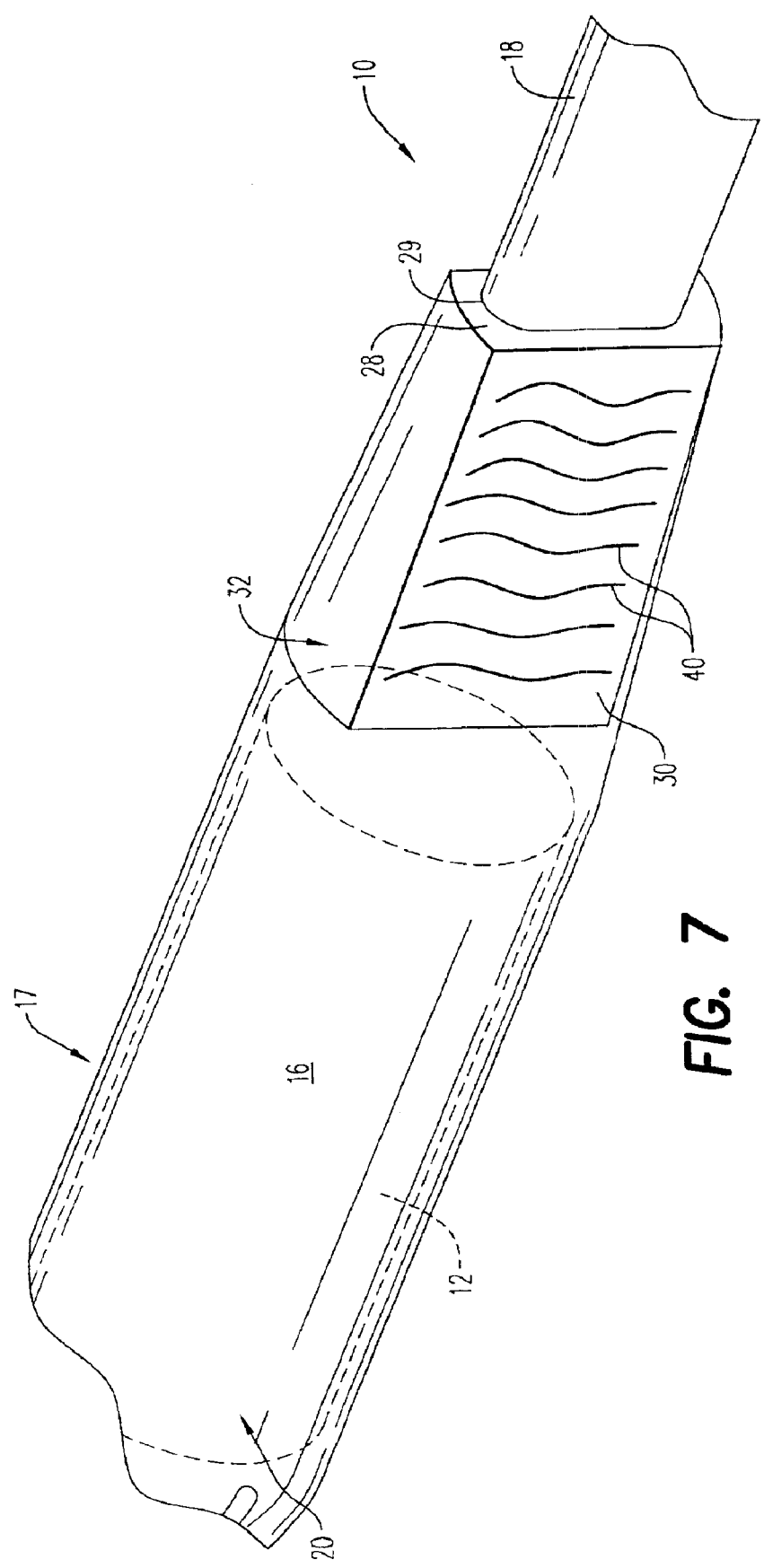
FIG. 7 is a perspective view of another embodiment of the tampon applicator of FIG. 1 having gripping structures according to the present invention.

Referring to FIG. 7, by way of example, another embodiment of the at least one gripping structure of tampon applicator 10 is depicted having a series of wavy gripping structures 40 disposed vertically across substantially flattened surfaces 30. The wavy gripping structures can also be raised above surfaces 30, depressed below surfaces 30, tilted towards and/or away from surfaces 30, or a combination thereof, and may be present in any suitable pattern or number.

Figure 8:
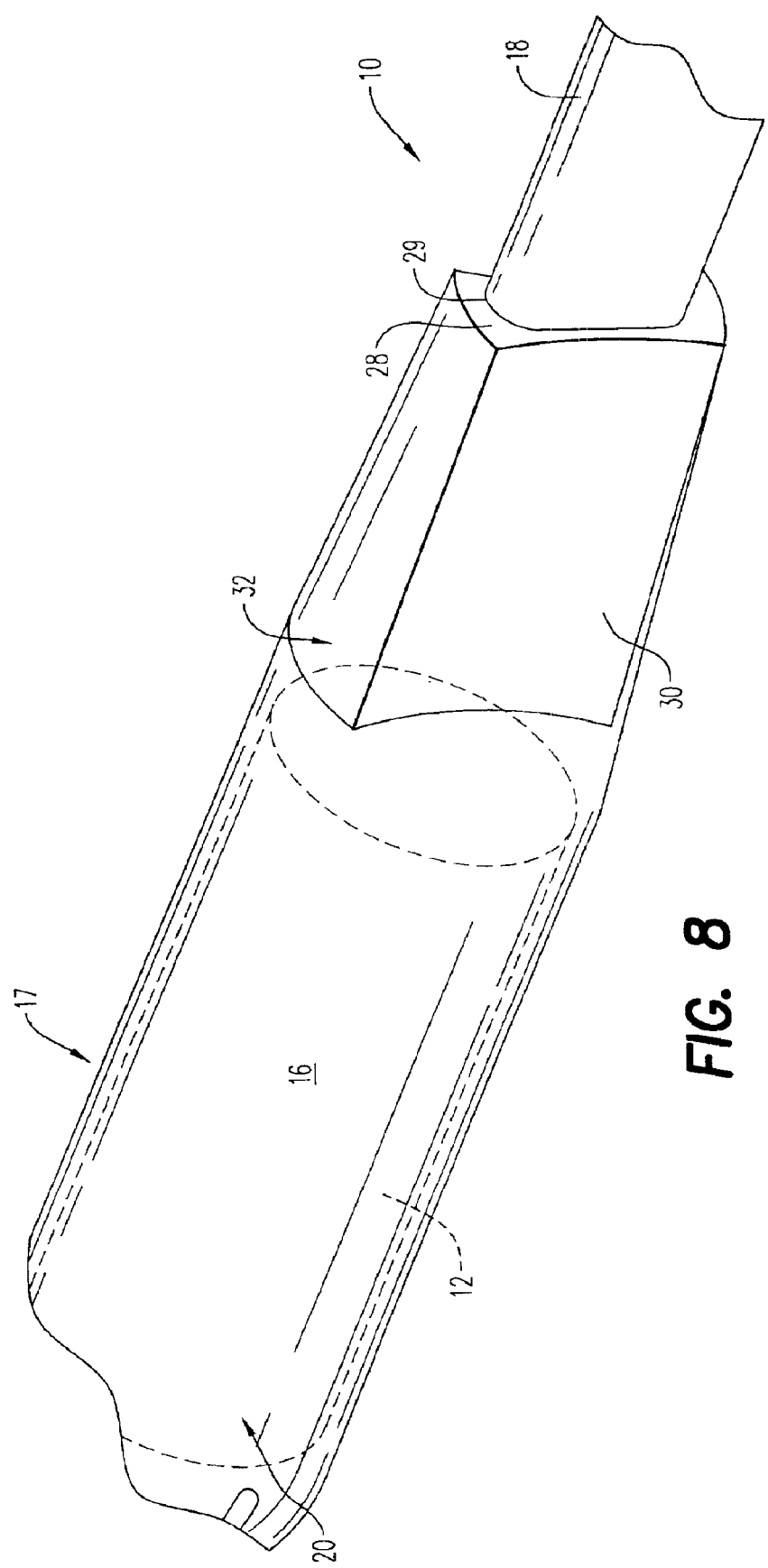
FIG. 8 is a perspective view of another embodiment of the tampon applicator of FIG. 1 having a concave fingergrip area according to the present invention.

Referring to FIG. 8, by way of example, another embodiment of the at least one gripping structure of tampon applicator 10 is depicted in which the surfaces 30 are formed with a concavity, thus providing an additional finger and/or thumb forming hold that conforms to a user's fingers.

Figure 9:
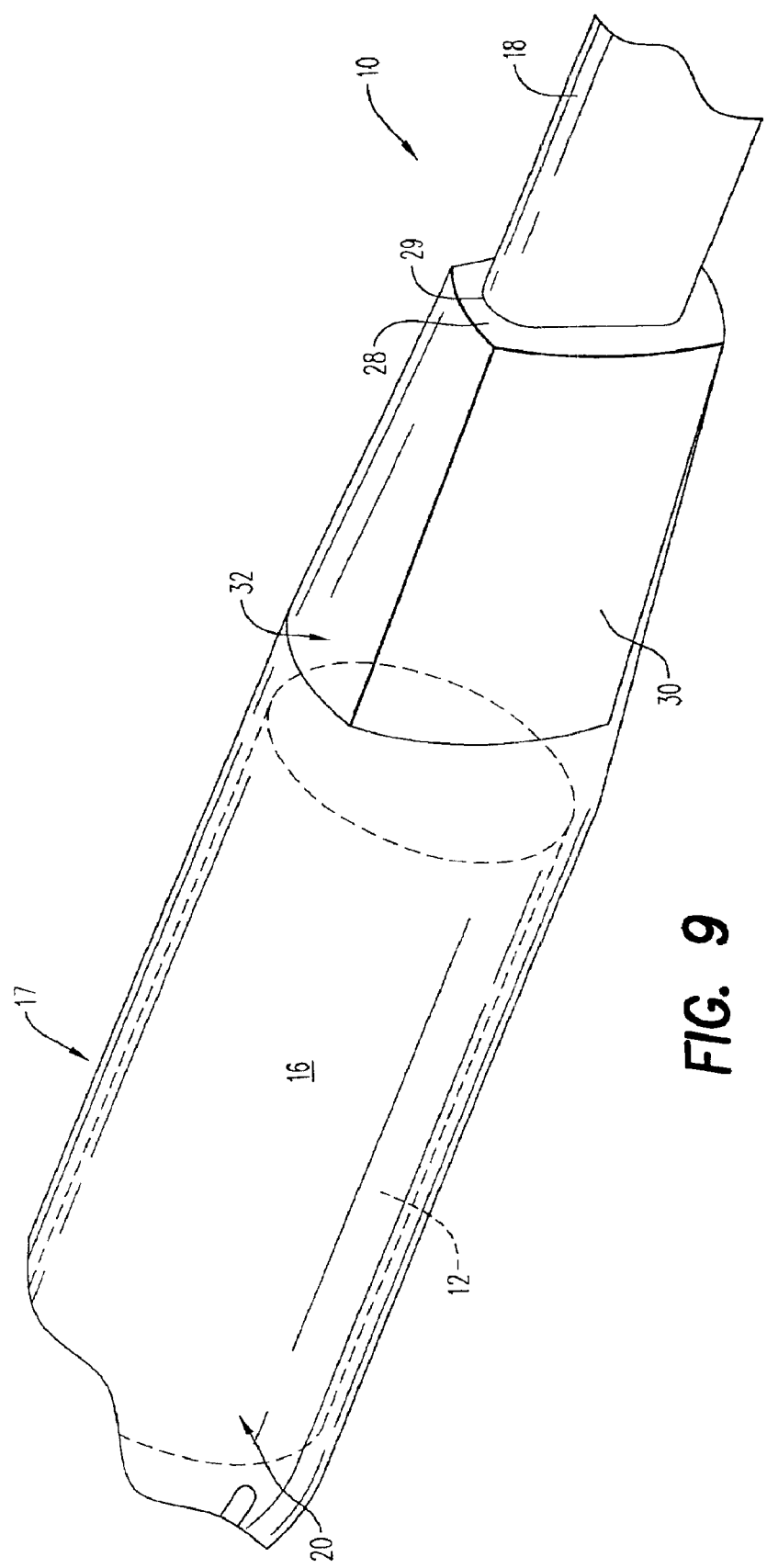
FIG. 9 is a perspective view of another embodiment of the tampon applicator of FIG. 1 having a convex fingergrip area according to the present invention.
Figure 10:
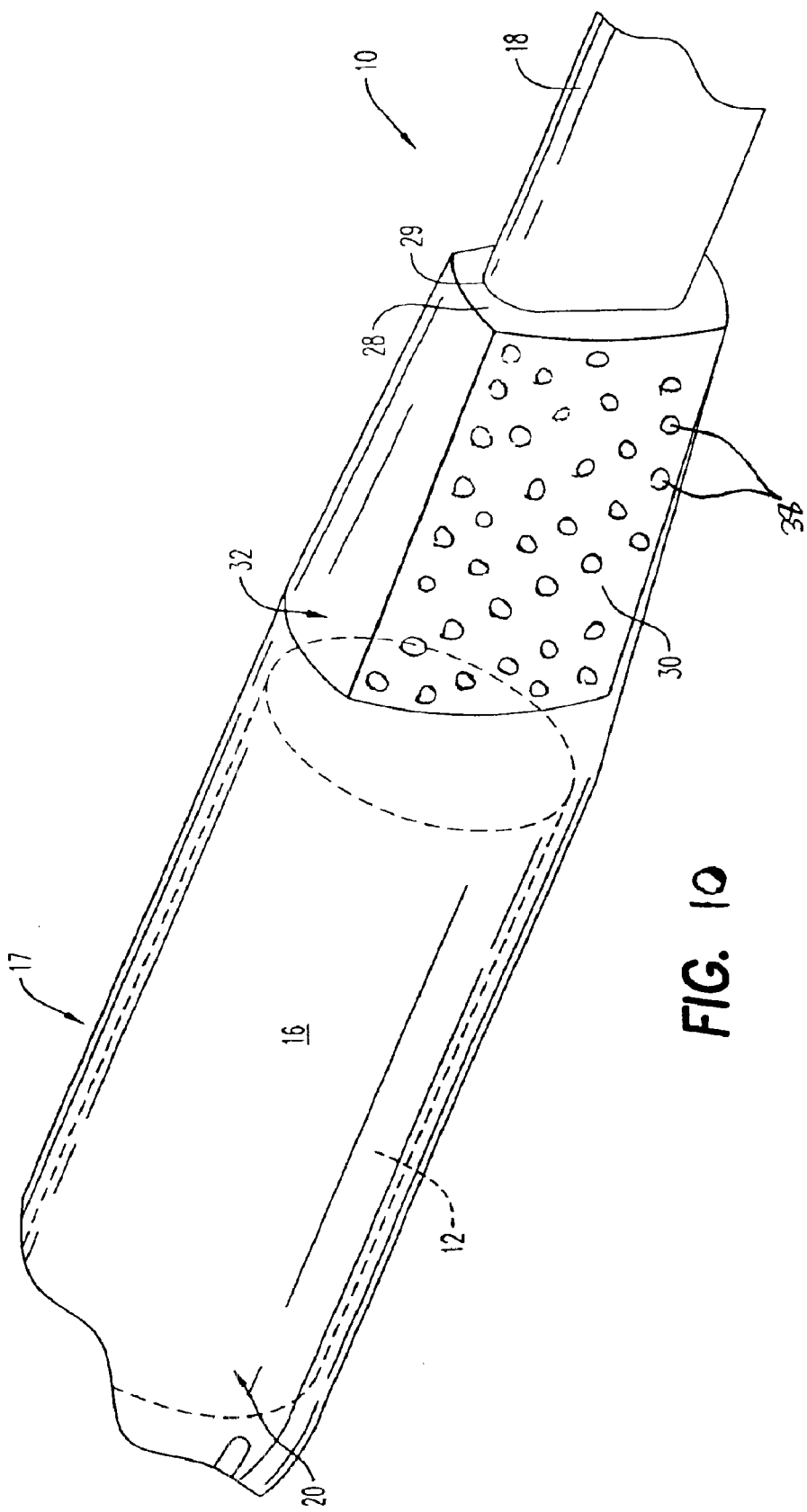
FIG. 10 is a perspective view of the tampon applicator of FIG. 9 with gripping structures according to an embodiment of the present invention.
Figure 11:
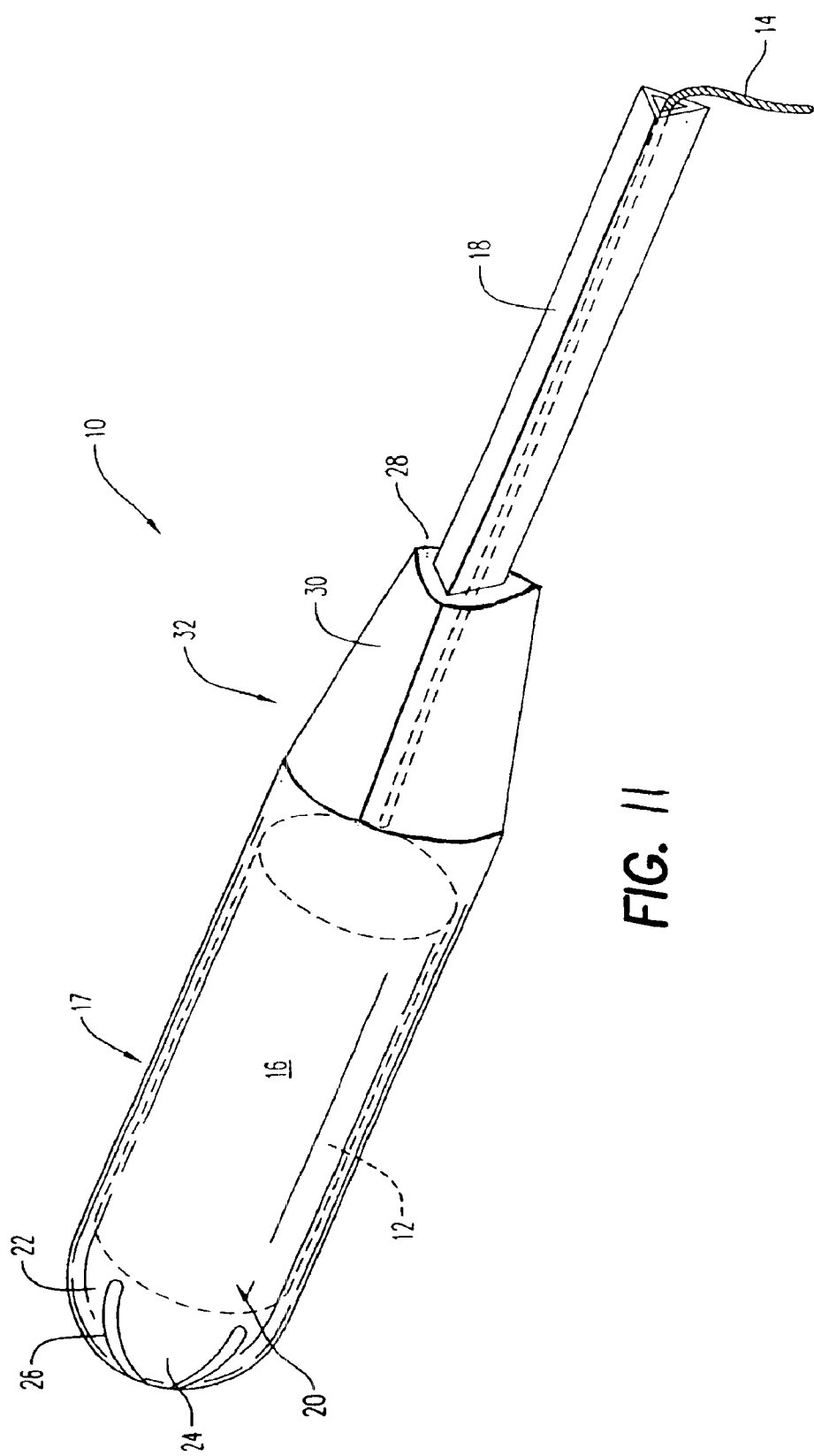
FIG. 11 is a perspective view of the tampon applicator of FIG. 4 with an odd number of convex surfaces according to an embodiment of the present invention.
Figure 12:
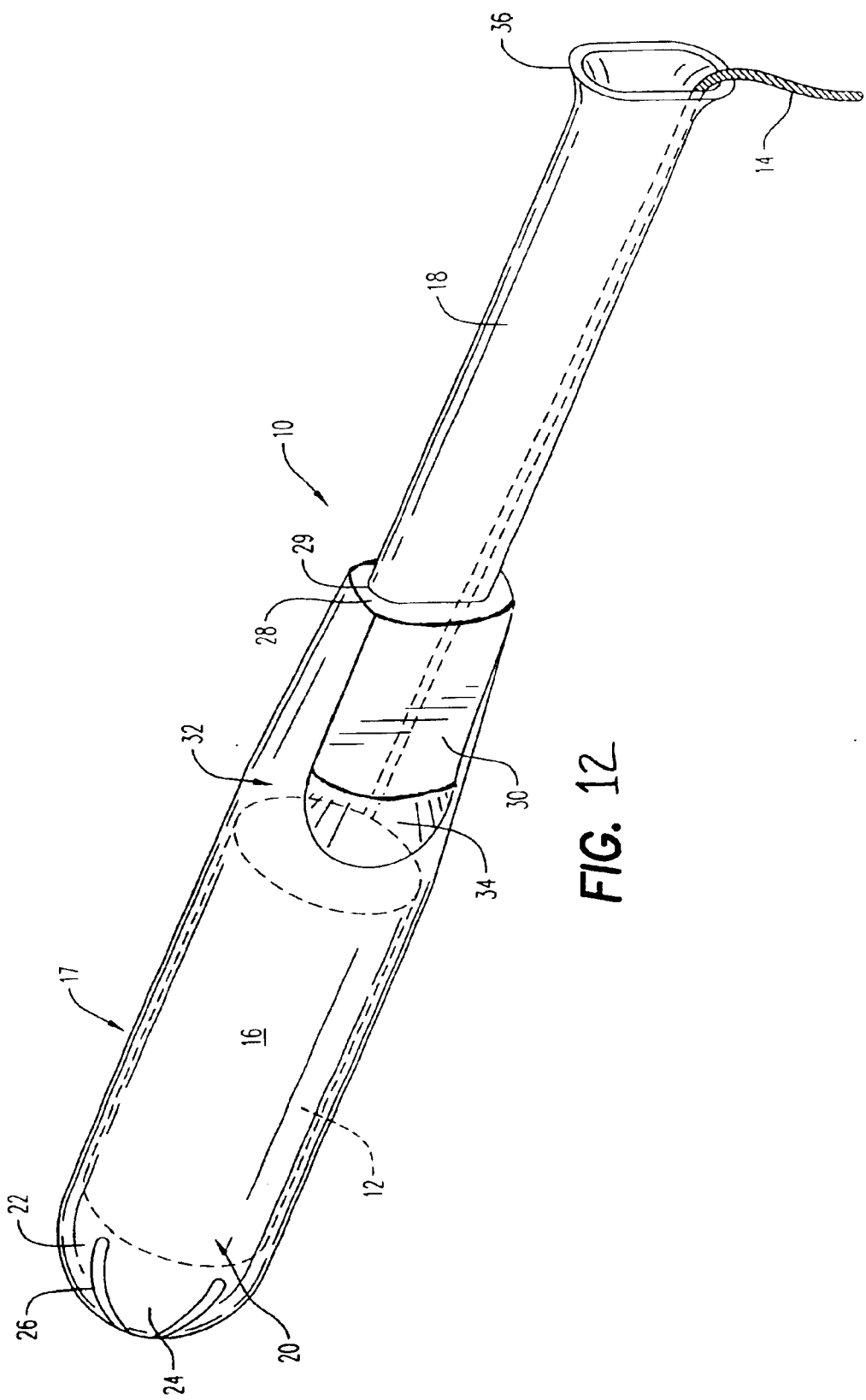
FIG. 12 is a perspective view of the tampon applicator of FIG. 5 with convex surfaces according to an embodiment of the present invention.

Referring to FIG. 9, by way of example, another embodiment of the at least one gripping structure of tampon applicator 10 is depicted in which the surfaces 30 are formed with a convex outer surface, thus providing an additional finger and/or thumb forming hold.

It should be understood that the embodiments shown in FIGS. 6 through 9, as well as all of the gripping structure embodiments described above, can be formed on the tampon applicator depicted in FIGS. 2 through 5, as well. This is illustrated by example in FIGS. 11, 12, 14 and 15.

The gripping structures may be created on surfaces 30 by any method known in the art, such as, for example, molding, embossing, laser engraving, taping, gluing, shearing, die punching, or any combinations thereof. Thus, by providing the receiving end 32 of the barrel 16 with a substantially flattened, and preferably also tapered, configuration and with at least one gripping structure, the receiving end serves as a superior grasping area, enabling the tampon user to easily and comfortably control and expel pledget 12 into the vagina.

The receiving end 32 is shown in FIGS. 1 through 5 as generally rectangular in cross-section to accommodate the flattened surfaces 30 thereof. Alternative cross-sectional shapes may be selected as long as such cross-sections accommodate the interior of surfaces 30 of the receiving end 32. Further, it should be understood that the cross-sectional areas of either end of the receiving end 32 do not necessarily need to be the same. For example, the examples shown in the figures have continued decreasing cross-sections from one end to the other. In addition, the cross-sections may reflect any concavities or convexities provided on the outer flattened surfaces 30 of the receiving end 32, to form an additional finger and/or thumb hold.

The receiving end 32 is also constructed to receive and axially engage the plunger 18 through an opening 29 therein. Accordingly, the general cross-sectional configuration of the receiving end 32 and the plunger edge 28, in particular, are preferably similar or comparable to that of the plunger 18 to accommodate smooth axial engagement between the barrel 16 and the plunger 18. Further, as in the preferred embodiment, the corners of the rectangular cross section of the receiving end 32 have some radius of curvature, which reduces any untoward frictional contact of the plunger 18 with the outer surfaces of the receiving end 32 and to enhance the aesthetic appearance of the applicator 10.

In another embodiment of the present invention, a curled lip 36 is provided on plunger 18, which provides a comfortable surface for resting the index finger in pushing the plunger forward to eject the pledget 12 from the barrel 16. The outer end of the plunger 18 may have other collar-like members or configurations such as an oval, circular cross-section or an arcuate finger rest that function in a like manner as the curled lip 36.

The tampon pledget 12, and notably radially expanding tampon pledgets, are capable of exerting forces on the applicator barrel 16, namely an inside surface of the applicator barrel. Such forces make it difficult for a tampon user to expel the pledget 12 from the applicator barrel 16.

With a radially expanding pledget, the expansion of the pledget may be, by design, immediate upon release from a tampon applicator, i.e. the expansion occurs entirely or primarily in its dry state, without the need for moisture or menses, or it may be an unintentional effect due to aging. Because of these radial-expansion characteristics, an increased force is exerted on the inside wall or surface of the applicator barrel 16. It has been found that the force may be as high as several times that of a conventional pledget that requires menses or moisture to expand. As a result of this pressure, an increased expulsion force is required to expel the pledget 12 from the barrel 16. Expulsion forces in the magnitude of 2.5 pounds and greater have been measured for radially expanding tampon pledgets. The high pledget expulsion force requires an applicator with such a distinct fingergrip as provided by the present invention, in order to hold the applicator without the fear of deforming the applicator barrel 16 and further impeding expulsion of the radially expanding pledget 12.

In summary, a woman can securely and comfortably grasp, control and position a tampon applicator 10 in accordance with the present invention, and expel a tampon pledget 12, especially a radially expanding pledget, housed therein, as a result of the fingergrip surface of the applicator 10, especially in conjunction with the at least one gripping structure formed on flattened surfaces 30.

Additionally, the gripping ability of a user can be further enhanced by forming diametrically opposed finger and/or thumb holds 34. By placing the user's middle finger and thumb on the flattened surfaces 30 of the rear portion 32 of the barrel 16 and set against the angled shoulders 34 of the barrel 16, the user is able to easily maneuver, control and position a tampon within her vagina, and expel a pledget into her vagina, without any excess muscle tension or strain that could result in deformation of the barrel and/or plunger.

The foregoing specification and drawings are merely illustrative of the present invention and are not intended to limit the present invention to the disclosed embodiments. Variations and changes, which are obvious to one skilled in the art, are intended to be within the scope and nature of the present invention as defined in the appended claims.

What is claimed is:

1. A tampon applicator comprising:
  a barrel adapted to house a pledget therein and to receive a plunger therein, said barrel having a fingergrip area adapted to partially house and engage said plunger, said fingergrip area having at least one substantially flattened surface, said at least one substantially flattened surface having at least one gripping structure other than a plurality of ribs or treads, wherein said fingergrip area has a reduced diameter relative to said barrel, wherein said at least one substantially flattened surface and said at least one gripping structure provide gripping ability to overcome ejection forces applied to said barrel by said pledget and/or said plunger.

2. The tampon applicator of claim 1, wherein said fingergrip area comprises at least one pair of diametrically opposed, substantially flattened surfaces.

3. The tampon applicator of claim 1, wherein said fingergrip area comprises an odd number of substantially flattened surfaces, and wherein at least one of said substantially flattened surfaces is diametrically opposed to a pair of adjoined substantially flattened surfaces.

4. The tampon applicator of claim 1, wherein said fingergrip area further comprises at least two angled shoulder surfaces.

5. The tampon applicator of claim 4, wherein said at least one substantially flattened surface is at least two substantially flattened surfaces, and wherein each of said at least two angled shoulder surfaces are disposed adjacent to each of said at least two substantially flattened surfaces on said fingergrip area.

6. The tampon applicator of claim 1, wherein said at least one gripping structure has a top in a plane that is raised above a plane having said at least one substantially flattened surface.

7. The tampon applicator of claim 1, wherein said at least one gripping structure is depressed below said at least one substantially flattened surface.

8. The tampon applicator of claim 1, wherein said at least one gripping structure is aligned with an outer surface of said at least one substantially flattened surface.

9. The tampon applicator of claim 1, wherein said at least one gripping structure has a position selected from the group consisting of tilted towards an outer surface of said at least one substantially flattened surface, tilted away from an outer surface of said at least one substantially flattened surface, and any combination thereof.

10. The tampon applicator of claim 1, wherein the tampon applicator further comprises a plunger, and wherein said plunger and said fingergrip area have substantially the same cross-sectional shape.

11. The tampon applicator of claim 10, wherein said cross-sectional shape is selected from the group consisting of: rectangular, square, triangular, or hexagonal.

12. The tampon applicator of claim 1, wherein said at least one gripping structure further comprises a plurality of ribs or treads.

13. The tampon applicator of claim 1, wherein said at least one gripping structure is patterned.

14. A tampon applicator comprising:
a barrel adapted to house a pledget therein and to receive a plunger therein, said barrel having a fingergrip area adapted to partially house and engage said plunger, said fingergrip area having at least one convex gripping surface, said at least one convex gripping surface having at least one gripping structure other than a plurality of ribs or treads, wherein said fingergrip area has a reduced diameter relative to said barrel, wherein said at least one convex gripping surface and said at least one gripping structure provide gripping ability to overcome ejection forces applied to said barrel by said pledget and/or said plunger.

15. The tampon applicator of claim 14, wherein said fingergrip area comprises at least one pair of diametrically opposed, convex gripping surfaces.

16. The tampon applicator of claim 14, wherein said fingergrip area comprises an odd number of convex gripping surfaces, and wherein at least one of said convex gripping surfaces is diametrically opposed to a pair of adjoined convex gripping surfaces.

17. The tampon applicator of claim 14, wherein said fingergrip area further comprises at least two angled shoulder surfaces.

18. The tampon applicator of claim 17, wherein said at least one convex gripping surface is at least two convex gripping surfaces, and wherein each of said at least two angled shoulder surfaces are disposed adjacent to each of said at least two convex gripping surfaces on said fingergrip area.

19. The tampon applicator of claim 14, wherein said at least one gripping structure is selected from the group consisting of embossments, protuberances, slits, grooves, louvers, perforations, lances, abrasive media, high wet coefficient of friction materials, pressure sensitive adhesives, and any combinations thereof.

20. The tampon applicator of claim 14, wherein said at least one gripping structure further comprises a plurality of ribs or treads.

21. The tampon applicator of claim 14, wherein said at least one gripping structure is patterned.

22. A tampon applicator comprising:
a barrel adapted to house a pledget therein and to receive a plunger therein, said barrel having a fingergrip area adapted to partially house and engage said plunger, said fingergrip area having at least one concave gripping surface, said at least one concave gripping surface having at least one gripping structure other than a plurality of ribs or treads, wherein said fingergrip area has a reduced diameter relative to said barrel, wherein said at least one concave gripping surface and said at least one gripping structure provide gripping ability to overcome ejection forces applied to said barrel by said pledget and/or said plunger.

23. The tampon applicator of claim 22, wherein said fingergrip area comprises at least one pair of diametrically opposed, concave gripping surfaces.

24. The tampon applicator of claim 22, wherein said fingergrip area comprises an odd number of concave gripping surfaces, and wherein at least one of said concave gripping surfaces is diametrically opposed to a pair of adjoined concave gripping surfaces.

25. The tampon applicator of claim 22, wherein said fingergrip area further comprises at least two angled shoulder surfaces.

26. The tampon applicator of claim 25, wherein said at least one concave gripping surface is at least two concave gripping surfaces, and wherein each of said at least two angled shoulder surfaces are disposed adjacent to each of said at least two concave gripping surfaces on said fingergrip area.

27. A tampon applicator comprising:
a barrel adapted to house a pledget therein and to receive a plunger therein, said barrel having a fingergrip area adapted to partially house and engage said plunger, said fingergrip area having an odd number of substantially flattened surfaces with at least one gripping structure selected from the group consisting of embossments, slits, perforations, lances, pressure sensitive adhesive, and any combinations thereof, wherein said fingergrip area has a reduced diameter relative to said barrel, wherein at least one of said substantially flattened surfaces is diametrically opposed to a pair of adjoined substantially flattened surfaces, and wherein said odd number of substantially flattened surfaces and said at least one gripping structure provide gripping ability to overcome ejection forces applied to said barrel by said pledget and/or said plunger.

28. A tampon applicator comprising:

a barrel adapted to house a pledget therein and to receive a plunger therein, said barrel having a fingergrip area adapted to partially house and engage said plunger, said fingergrip area having at least one substantially flattened surface with at least one gripping structure selected from the group consisting of embossments, slits, perforations, lances, pressure sensitive adhesive, and any combinations thereof, wherein said fingergrip area has a reduced diameter relative to said barrel, wherein said at least one gripping structure is depressed below said at least one substantially flattened surface, and wherein said at least one substantially flattened surface and said at least one gripping structure provide gripping ability to overcome ejection forces applied to said barrel by said pledget and/or said plunger.

29. A tampon applicator comprising:

a barrel adapted to house a pledget therein and to receive a plunger therein, said barrel having a fingergrip area adapted to partially house and engage said plunger, said fingergrip area having an odd number of convex gripping surfaces with at least one gripping structure, wherein said fingergrip area has a reduced diameter relative to said barrel, wherein at least one of said convex surfaces is diametrically opposed to a pair of adjoined convex surfaces, and wherein said odd number of convex gripping surfaces and said at least one gripping structure provide gripping ability to overcome ejection forces applied to said barrel by said pledget and/or said plunger.

30. A tampon applicator comprising:

a barrel adapted to house a pledget therein and to receive a plunger therein, said barrel having a fingergrip area adapted to partially house and engage said plunger, said fingergrip area having an odd number of concave gripping surfaces with at least one gripping structure selected from the group consisting of embossments, slits, perforations, lances, pressure sensitive adhesives, and any combinations thereof, wherein said fingergrip area has a reduced diameter relative to said barrel, wherein at least one of said concave gripping surfaces is diametrically opposed to a pair of adjoined concave gripping surfaces, and wherein said odd number of concave gripping surfaces and said at least one gripping structure provide gripping ability to overcome ejection forces applied to said barrel by said pledget and/or said plunger.

31. The tampon applicator of claim 22, wherein said at least one gripping structure further comprises a plurality of ribs or treads.

32. The tampon applicator of claim 22, wherein said at least one gripping structure is patterned.

* * * * *

(12) INTER PARTES REEXAMINATION CERTIFICATE (879th)
United States Patent
Jackson et al.

(10) Number: US 6,890,324 C1
(45) Certificate Issued: May 16, 2014

(54) TAMPON APPLICATOR

(75) Inventors: Dane R. Jackson, Bloomingdale, NJ (US); Paul A. Siracusa, Florida, NY (US); Keith Edgett, Ramsey, NJ (US)

(73) Assignee: GE Canada Finance Holding Company, Toronto, Ontario (CA)

Reexamination Request:
No. 95/001,654, Jun. 10, 2011

Reexamination Certificate for:
Patent No.: 6,890,324
Issued: May 10, 2005
Appl. No.: 09/894,042
Filed: Jun. 28, 2001

(51) Int. Cl.
*A61F 13/20* (2006.01)

(52) U.S. Cl.
USPC ..................................... 604/385.17; 604/904

(58) Field of Classification Search
None
See application file for complete search history.

(56) References Cited

To view the complete listing of prior art documents cited during the proceeding for Reexamination Control Number 95/001,654, please refer to the USPTO's public Patent Application Information Retrieval (PAIR) system under the Display References tab.

*Primary Examiner* — Catherine S. Williams

(57) ABSTRACT

A tampon is provided having an applicator barrel adapted to house a pledget, and especially a radially expanding pledget, and receive a telescoping plunger that is adapted to expel the pledget from the barrel. The applicator barrel has a fingergrip area with at least one set of diametrically opposed, substantially flattened surfaces, convex surfaces, concave surfaces, or any combination thereof. These surfaces have at least one gripping structure to enhance the gripping characteristics of the applicator, allowing the user to securely hold the applicator during insertion and removal and during expulsion of the pledget from the barrel.

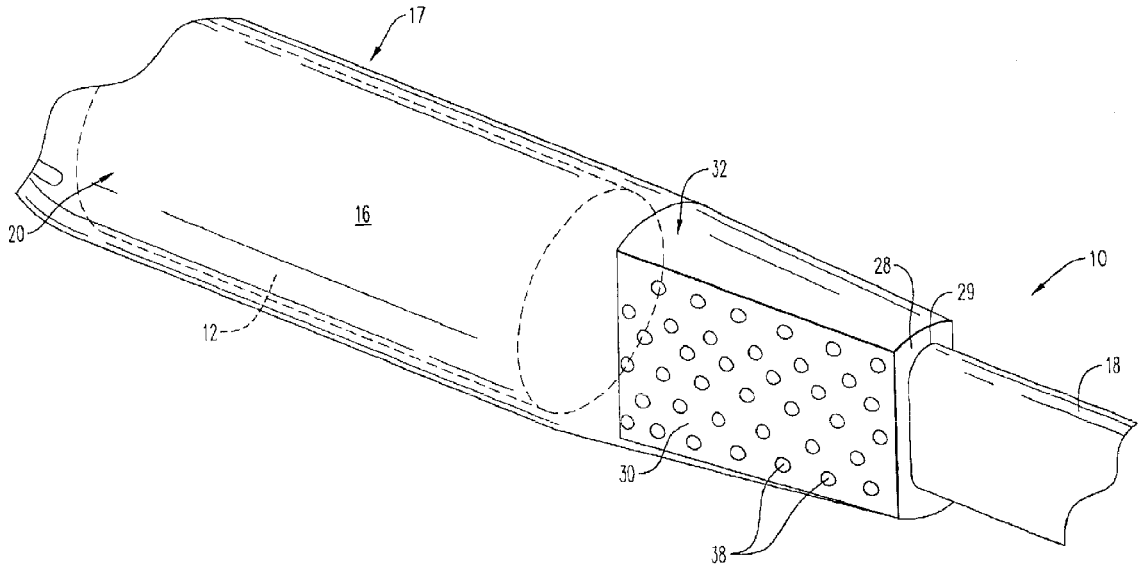

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-32 are cancelled.

* * * * *